(12) United States Patent
Ogawa

(10) Patent No.: US 6,783,495 B2
(45) Date of Patent: Aug. 31, 2004

(54) ULTRASONIC DIAGNOSING APPARATUS

(75) Inventor: Eiji Ogawa, Kaisei-machi (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/388,457

(22) Filed: Mar. 17, 2003

(65) Prior Publication Data

US 2003/0181813 A1 Sep. 25, 2003

(30) Foreign Application Priority Data

Mar. 19, 2002 (JP) ....................................... 2002-075512

(51) Int. Cl.[7] .............................................. A61B 8/00
(52) U.S. Cl. ...................................................... 600/437
(58) Field of Search ................................. 600/407–472; 601/2, 3; 367/7, 11, 130; 73/625, 626; 378/42–65, 98.8

(56) References Cited

U.S. PATENT DOCUMENTS

| | | | | |
|---|---|---|---|---|
| 4,819,255 A | * | 4/1989 | Sato | ............................ 378/42 |
| 5,884,627 A | * | 3/1999 | Wakabayashi et al. | ...... 600/447 |
| 6,222,906 B1 | * | 4/2001 | Sakaguchi et al. | ......... 378/98.8 |
| 6,307,914 B1 | * | 10/2001 | Kunieda et al. | .............. 378/65 |
| 6,540,700 B1 | * | 4/2003 | Fujimoto et al. | .............. 601/3 |

* cited by examiner

*Primary Examiner*—Ali Imam
(74) *Attorney, Agent, or Firm*—Sughrue Mion, PLLC

(57) ABSTRACT

In an ultrasonic diagnosing apparatus, a total amount of ultrasonic waves which irradiate an object to be inspected for a constant time period can be decreased, while image qualities of ultrasonic images are not deteriorated. The ultrasonic diagnosing apparatus includes an ultrasonic transmitting/receiving unit for transmitting ultrasonic waves in accordance with an applied voltage and receiving ultrasonic echoes reflected from an object to be inspected; an input unit for inputting information related to an irradiation amount of ultrasonic waves; and an irradiation amount control unit for adjusting a frame rate on the basis of the irradiation amount information input via the input unit so as to control an irradiation amount of ultrasonic waves which irradiate the object.

14 Claims, 9 Drawing Sheets

10

TO MAIN BODY OF ULTRASONIC DIAGNOSING APPARATUS

ULTRASONIC DIAGNOSING APPARATUS

BACKGROUND OF THE INVENTION

1. Field of the Invention

The present invention is related to an ultrasonic diagnosing apparatus used so as to perform medical diagnosing operations by transmitting ultrasonic waves toward an object to be inspected, and by receiving ultrasonic echoes reflected from the object.

2. Description of a Related Art

In medical fields, various types of imaging techniques have been developed in order to observe and diagnose interior portions of an object to be inspected. In particular, as to ultrasonic imaging techniques capable of acquiring internal information of an object to be inspected by transmitting/receiving ultrasonic waves to/from the object, ultrasonic image observations can be carried out in real time, and furthermore, there is no risk that the object is exposed by radioactive rays, which is different from other medical imaging techniques using X-ray photography, RI (radio isotope) scintillation cameras or the like. As a consequence, the ultrasonic imaging techniques are utilized as imaging techniques having higher safety characteristics in very broad fields which may involve the obstetrics and gynecology department, the circulatory organ department and the digestive department as well as fetus diagnosis in the obstetrical department.

However, in an actual case, there are many unknown aspects with respect to adverse influences caused by ultrasonic waves given to biological bodies. For example, as techniques using energy of ultrasonic waves, the following methods are known. That is, in a cure, cancerous cells of biological bodies are destroyed by employing strong focused ultrasonic waves. In an ultrasonic homogynizer, cavitation is generated by employing strong focused ultrasonic waves so as to stir or crash samples. In a heat-curing device, heating effect achieved by ultrasonic waves are utilized. While such a nature of ultrasonic waves is considered, even when very weak ultrasonic waves are utilized in ultrasonic imaging operations, or even when high frequency ultrasonic waves are utilized, a certain adverse influence given to biological bodies may be predicted. Also, according to current research reports, ultrasonic examinations executed while woman is pregnant may give adverse influences to the fetus. As a result, it is preferable that intensity of ultrasonic waves which irradiate the object during ultrasonic imaging operations must be suppressed to minimum necessary intensity.

By the way, in an ultrasonic imaging operation, an irradiation intensity of ultrasonic waves is expressed by an MI (medical index value). In recent general-purpose ultrasonic diagnosing apparatus, such a function is provided by which irradiation intensity of ultrasonic waves is controlled by setting the MI value. However, the adverse influences of ultrasonic waves to the biological bodies are caused not only by intensity of these ultrasonic waves. For instance, the previously-explained heating effect of ultrasonic waves is related to the ultrasonic irradiation amount which is obtained both the intensity of ultrasonic waves and the irradiation time thereof.

An ultrasonic irradiation amount is also changed depending upon a scanning method employed when an ultrasonic imaging operation is carried out. For instance, in an M-mode imaging operation, since ultrasonic waves continuously irradiate one portion, a total ultrasonic irradiation amount at the same portion of a biological body is increased. In contrast, in a B-mode imaging operation, although this imaging operation requires long operation time, since an irradiation direction of ultrasonic waves is always changed, a total ultrasonic irradiation amount at one portion is small. Furthermore, in accordance with a color Doppler mode, since ultrasonic waves having high intensity irradiate the object along the same direction many times, an entire ultrasonic irradiation amount is increased.

As previously explained in the case where adverse influences of ultrasonic waves to an object to be inspected are considered, there is an important aspect. That is, not only intensity of these ultrasonic waves, but also a total amount of ultrasonic waves which irradiate the object for a constant time period must be considered. However, conventionally, such an ultrasonic diagnosing apparatus capable of counting an ultrasonic irradiation amount or capable of controlling such an ultrasonic irradiation amount has not yet been developed. Also, when an MI value is set to a lower MI value in order to suppress an ultrasonic irradiation amount, intensity of a received signal is also lowered. As a result, there is a problem that an S/N ratio in ultrasonic images is also uniformly lowered, so that the image qualities are deteriorated.

SUMMARY OF THE INVENTION

The present invention has been made to solve the above-described problems, and therefore, has an object to provide such an ultrasonic diagnosing apparatus capable of decreasing a total amount of ultrasonic waves which irradiate an object to be inspected for a constant time period, while image qualities of ultrasonic images are not deteriorated.

To solve the above-described problem, an ultrasonic diagnosing apparatus according to a first aspect of the present invention comprises: ultrasonic transmitting and receiving means for transmitting ultrasonic waves in accordance with an applied voltage and receiving ultrasonic echoes reflected from an object to be inspected; input means for inputting information related to an irradiation amount of ultrasonic waves; and irradiation amount control means for adjusting a frame rate on the basis of the irradiation amount information input via the input means so as to control an irradiation amount of ultrasonic waves which irradiate the object.

Here, the frame rate corresponds to a transmission rate of ultrasonic waves which are transmitted plural times in order to acquire ultrasonic images, and is expressed by a number of frames acquired per second.

In accordance with the first aspect of the present invention, since the ultrasonic irradiation amount is controlled not by adjusting the irradiation intensity but by adjusting the frame rate, the ultrasonic irradiation amount can be suppressed to a lower ultrasonic irradiation amount without deteriorating image qualities.

Further, an ultrasonic diagnosing apparatus according to a second aspect of the present invention comprises: ultrasonic transmitting and receiving means for transmitting ultrasonic waves in accordance with an applied voltage and receiving ultrasonic echoes reflected from an object to be inspected; accumulating means for accumulating an irradiation amount of ultrasonic waves transmitted from the ultrasonic transmitting and receiving means to obtain an accumulated value; and irradiation amount control means for adjusting a frame rate on the basis of a relationship between the accumulated value obtained by the accumulating means and a preset value so as to control an irradiation amount of ultrasonic waves which irradiate the object.

According to the second aspect of the present invention, while the ultrasonic imaging operation is carried out, the ultrasonic irradiation amount is accumulated. When the accumulated value reaches a preset value, the frame rate is lowered, so that it is possible to avoid excessive irradiation of ultrasonic waves.

In this application, an ultrasonic irradiation amount implies such a value which is obtained by integration intensity of ultrasonic waves irradiating an object to be inspected by time.

BRIEF DESCRIPTION OF THE DRAWINGS

A better understanding of the present invention may be achieved by reading a detailed description in conjunction with the accompanying drawings, in which.

DESCRIPTION OF THE PREFERRED EMBODIMENTS

Figure 1:
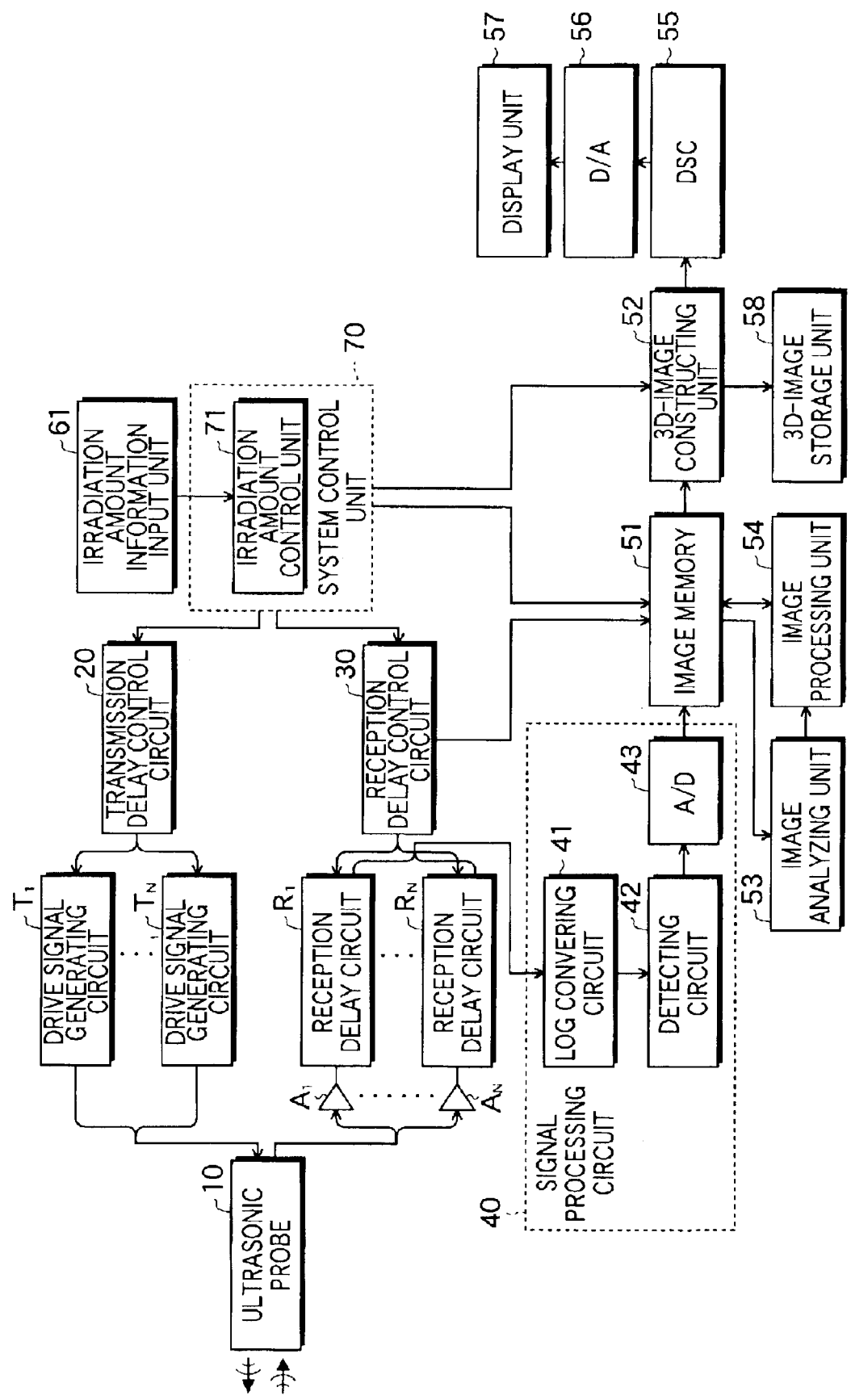
FIG. 1 is a block diagram for schematically showing an arrangement of an ultrasonic diagnosing apparatus according to a first embodiment of the present invention.

Referring now to drawings, various embodiments of the present invention will be described in detail. It should be understood that the same reference numerals will be employed as those for denoting the same or similar structural elements, and descriptions thereof are omitted.

FIG. 1 is a schematic block diagram for showing an arrangement of an ultrasonic diagnosing apparatus according to a first embodiment of the present invention. This ultrasonic diagnosing apparatus includes an ultrasonic probe 10. This ultrasonic probe 10 transmits ultrasonic waves toward an object to be inspected, and then, receives ultrasonic echoes which return by being reflected from the object. The ultrasonic probe 10 includes an ultrasonic transducer array in which a plurality of ultrasonic transducers for transmitting ultrasonic waves and receiving ultrasonic echoes are arrayed.

Figure 2:
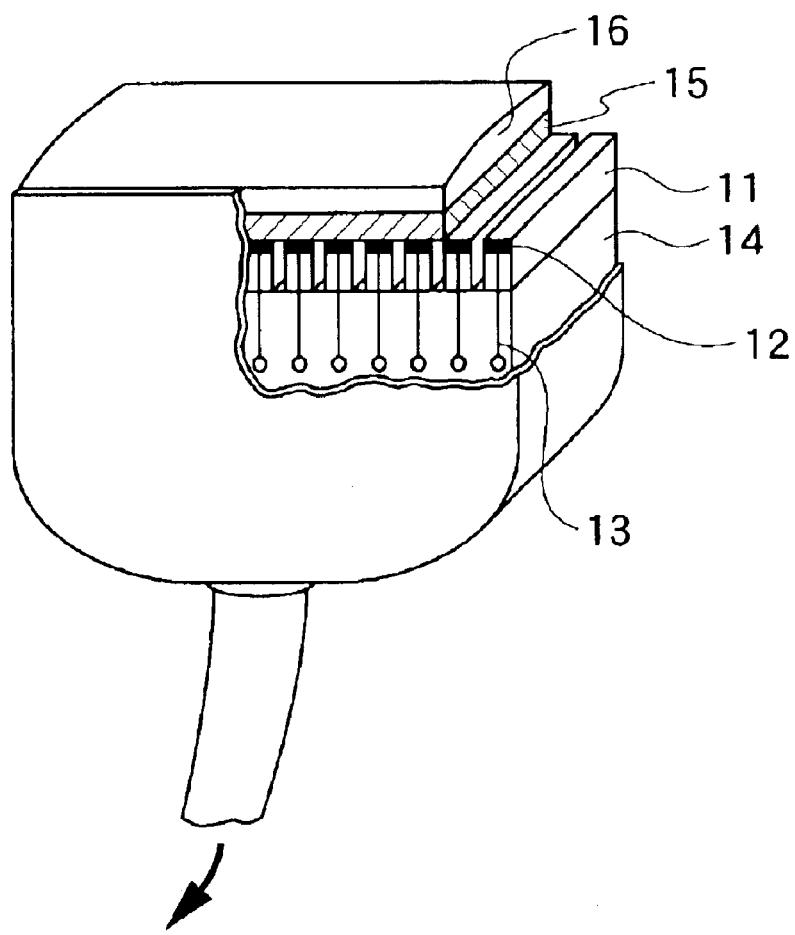
FIG. 2 is a diagram for illustratively showing a structure of an ultrasonic probe as shown in FIG. 1.

FIG. 2 illustratively shows a structure of the above-described ultrasonic probe 10. As ultrasonic transducers, N pieces of vibrating elements 11 are employed, each includes piezoelectric ceramics typically known as PZT (Pb(lead) zirconate titanate) or macromolecular piezoelectric elements typically known as PVDF (polyvinyl difluoride). Electrodes 12 are mounted on these vibrating elements 11 respectively, and these electrodes 12 are connected via lead wires 13 to an electronic circuit provided in a main body of the ultrasonic diagnosing apparatus. Further, the ultrasonic probe 10 may include a backing member 14, an acoustic matching layer 15, an acoustic lens 16, and so on. The backing member 14 supports the vibrating elements 11 and acoustically brakes these vibrating elements 11. The acoustic matching layer 15 makes the ultrasonic waves be transmitted in a high efficiency. The acoustic lens 16 is used to focus the ultrasonic waves.

The vibrating elements 11 are employed as a transmission element for transmitting ultrasonic waves in accordance with drive signals transferred via the lead wires 13, and also are employed as a receiving element for receiving ultrasonic echoes and converting the received ultrasonic echoes into electric signals. Although the same transmitting/receiving type ultrasonic transducers such as the vibrating elements 11 are employed in the first embodiment, piezoelectric type vibrating elements may be employed as the transmission elements while any type other than piezoelectric type ultrasonic transducers may be employed as the receiving elements. As any type other than piezoelectric type ultrasonic transducer, for instance, an optical detecting type ultrasonic transducer may be employed which modulates light on the basis of ultrasonic waves received by this ultrasonic transducer. This optical detecting type ultrasonic transducer is described more in detail in, for example, "Underwater Acoustic Sensor with Fiber Bragg Grating" written by TAKAHASHI et al. of National Defense Academy Japan, OPTICAL REVIEW Vol. 4, No. 6, 1997, pages 691 to 694 and "Fabrication and Performance of a Fiber Optic Micro-Probe for Megahertz Ultrasonic Field Measurement" written by UNO et al. of Tokyo Institute of Technology, T. IEE Japan, Vol. 118-E, No. 11, 1998.

Also, in FIG. 2, such a linear array type ultrasonic probe is illustrated in which a plurality of vibrating elements 11 are arrayed on a plane in a one-dimensional manner. Moreover, in the first embodiment, ultrasonic probes in which vibrating elements are arranged in various modes may be employed. For example, a concave type ultrasonic probe in which a plurality of vibrating elements are arranged on a concave plane may be alternatively employed. Also, a convex array type ultrasonic probe in which a plurality of vibrating elements are arranged on a convex plane may be alternatively employed. Further, an annular type ultrasonic probe in which annular-shaped vibrating elements are arranged in a coaxial shape may be employed.

Referring back to FIG. 1, this ultrasonic diagnosing apparatus includes a transmission delay control circuit 20, N pieces of drive signal generating circuits $T_1$ to $T_N$, N pieces of amplifiers $A_1$ to $A_N$, N pieces of reception delay circuits $R_1$ to $R_N$, and a reception delay control circuit 30. The drive signal generating circuits $T_1$ to $T_N$ generate drive signals to be output to a plurality of vibrating elements included in the ultrasonic probe 10. The transmission delay control circuit 20 controls delay times produced in the drive signal generating circuits $T_1$ to $T_N$ in order that one or more ultrasonic beam is transmitted from the ultrasonic probe 10. The amplifiers $A_1$ to $A_N$ amplify detection signals output from the ultrasonic probe 10. The reception delay circuits $R_1$ to $R_N$ apply time delays to the amplified detection signals so as to adjust phases of the detection signals under control of the reception delay control unit 30.

Further, this ultrasonic diagnosing apparatus includes a signal processing unit 40 having a log (logarithm) converting circuit 41, a detection circuit 42, and an A/D converter 43. The signal processing unit 40 executes such signal processing as a logarithm compression, an amplitude detection and an A/D (analog to digital) conversion with respect to detection signals output from the reception delay circuits $R_1$ to $R_N$.

Furthermore, this ultrasonic diagnosing apparatus includes an image memory 51, a 3D (three-dimensional) image constructing unit 52, an image analyzing unit 53, an image processing unit 54, a DSC (digital scan converter) 55, a D/A converter 56 and a display unit 57. The image memory 51 stores thereinto output data of the signal processing unit 40 every frame. The 3D image constructing unit 52 executes calculation processing with respect to the frame data stored in the image memory 51 so as to produce synthesized image data. Both the image analyzing unit 53 and the image processing unit 54 analyze the frame data stored in the image memory 51 and perform such image processing as an interpolation, a response modulating process and a gradation process. Both the DSC 55 and the D/A converter 56 execute data conversion processing on the basis of image data constructed in the 3D image constructing unit 52, so that data for display purposes is produced. The display unit 57 includes such a display apparatus as a CRT (cathode-ray tube) or an LCD (liquid crystal display), and displays thereon an image on the basis of the produced display data. In addition, this ultrasonic diagnosing apparatus may include a 3D-image storage unit 58 for storing thereinto the constructed image data.

This ultrasonic diagnosing apparatus owns an irradiation amount input unit 61 including an input device such as an adjusting knob, a touch panel or the like. Here, irradiation amount information implies numerical information employed so as to control an irradiation amount of ultrasonic waves which irradiate an object to be inspected for a predetermined time period. As a method of inputting this irradiation amount information, for instance, the adjusting knob may be controlled in order to point out a desirable value so that a numerical value representative of an ultrasonic irradiation amount can be input. Alternatively, various information related to an object to be inspected involving, for example, an age, a build and a body portion to be irradiated by ultrasonic waves may input by manipulating a touch panel so that a numerical value indicative of an ultrasonic irradiation amount can be calculated. In this alternative case, it is preferable to further provide both a storage unit for storing thereinto a relationship between the information related to the object and the irradiation amount information, and also, a calculation unit for calculating a minimum necessary value of the ultrasonic irradiation amount.

The system control unit 70 controls the above-mentioned structural units of this ultrasonic diagnosing apparatus. Further, the system control unit 70 includes an irradiation amount control unit 71. The irradiation amount control unit 71 controls a transmission pulse interval on the basis of irradiation amount information, which is input by employing the irradiation amount input unit 61, so that a frame rate can be adjusted. Here, the irradiation amount control unit 71 may set the frame rate on the basis of such a numerical value input as the irradiation amount information, or such information related to the object to be inspected. In the latter case, it is preferable that such a table for defining a corresponding relation between frame rates and information related to objects to be inspected is previously prepared and stored.

Figure 3:
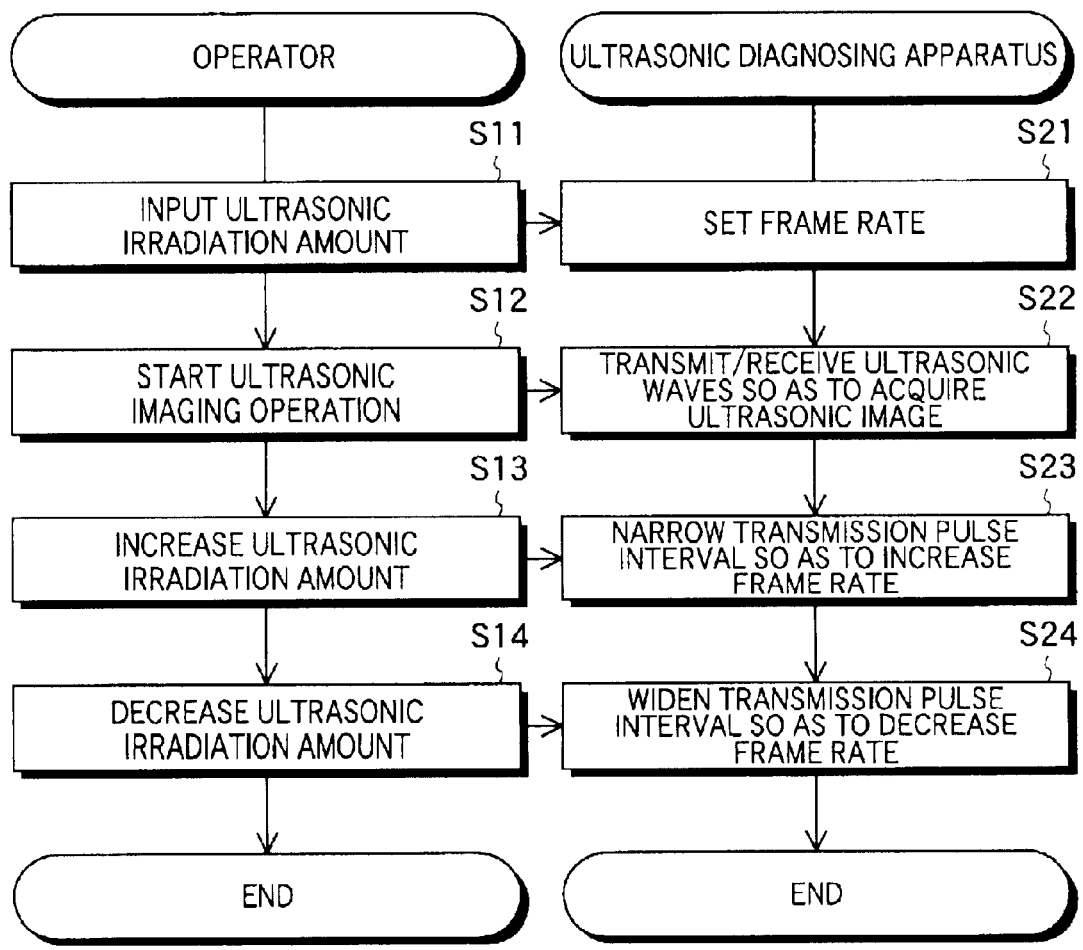
FIG. 3 is a flow chart for showing operations of the ultrasonic diagnosing apparatus as shown in FIG. 1.

Next, operations of the ultrasonic diagnosing apparatus according to the first embodiment will now be explained. FIG. 3 is a flow chart for showing operations of both an operator and this ultrasonic diagnosing apparatus when performing ultrasonic imaging of an object to be inspected.

First, the operator inputs irradiation amount information by employing the irradiation amount information input unit 61 of this ultrasonic diagnosing apparatus at step S11 of this flow chart. In this case, a total amount of ultrasonic waves which is allowed to irradiate the object differs depending upon ages, builds, body portions of the object irradiated by the ultrasonic waves. Therefore, a minimum necessary value of the irradiation amount may be preferably set in accordance with these conditions. Otherwise, information related to the object such as ages, builds and so on may be input so that a proper irradiation amount value is obtained.

At step S21, the irradiation amount control unit 71 of the ultrasonic diagnosing apparatus sets a frame rate on the basis of the input irradiation amount information.

When the operator commences ultrasonic imaging operation at step S12, the ultrasonic diagnosing apparatus transmits ultrasonic waves and then receives ultrasonic echoes so as to acquire an ultrasonic image of the object to be inspected at step S22.

There may be a case where a more precise ultrasonic image is required while the object is scanned by employing the ultrasonic probe 10. In such a case, the operator increases the ultrasonic irradiation amount by adjusting the irradiation amount information input unit 61 at step S13. In accordance with this control, the irradiation amount control unit 71 narrows the transmission pulse interval so as to increase the frame rate at step S23. As a result, a more precise ultrasonic image may be acquired.

At step S14, the operator adjusts the irradiation amount information input unit 61 so as to decrease the ultrasonic irradiation amount after the ultrasonic probe 10 has passed through a region where detailed image information is required. Otherwise, the operator adjusts the irradiation amount information input unit 61 so as to decrease the ultrasonic irradiation amount while a not-important region is scanned or while a region, which becomes risky when an ultrasonic irradiation amount is large, is scanned by employing the ultrasonic probe 10. In response to this decreased ultrasonic irradiation amount, the irradiation amount control unit 71 widens the transmission pulse interval so as to lower the frame rate at step S24. As a result, an increase of the ultrasonic irradiation amount may be suppressed.

According to the first embodiment, the irradiation amount of ultrasonic waves, which irradiate the object to be inspected, is controlled not by adjusting the irradiation intensity, but by adjusting the frame rate. As a result, even when the ultrasonic irradiation amount is suppressed, the ultrasonic images having better image qualities can be acquired without decreasing the S/N ratio achieved in the ultrasonic waves per frame. Also, while the object is scanned, the operator can adjust the irradiation amount of ultrasonic waves by judging whether or not a body portion imaged at that time is too important to obtain detailed image information. As a consequence, the ultrasonic imaging operations can be effectively carried out, while the ultrasonic irradiation amount with respect to the object can be suppressed.

Figure 4:
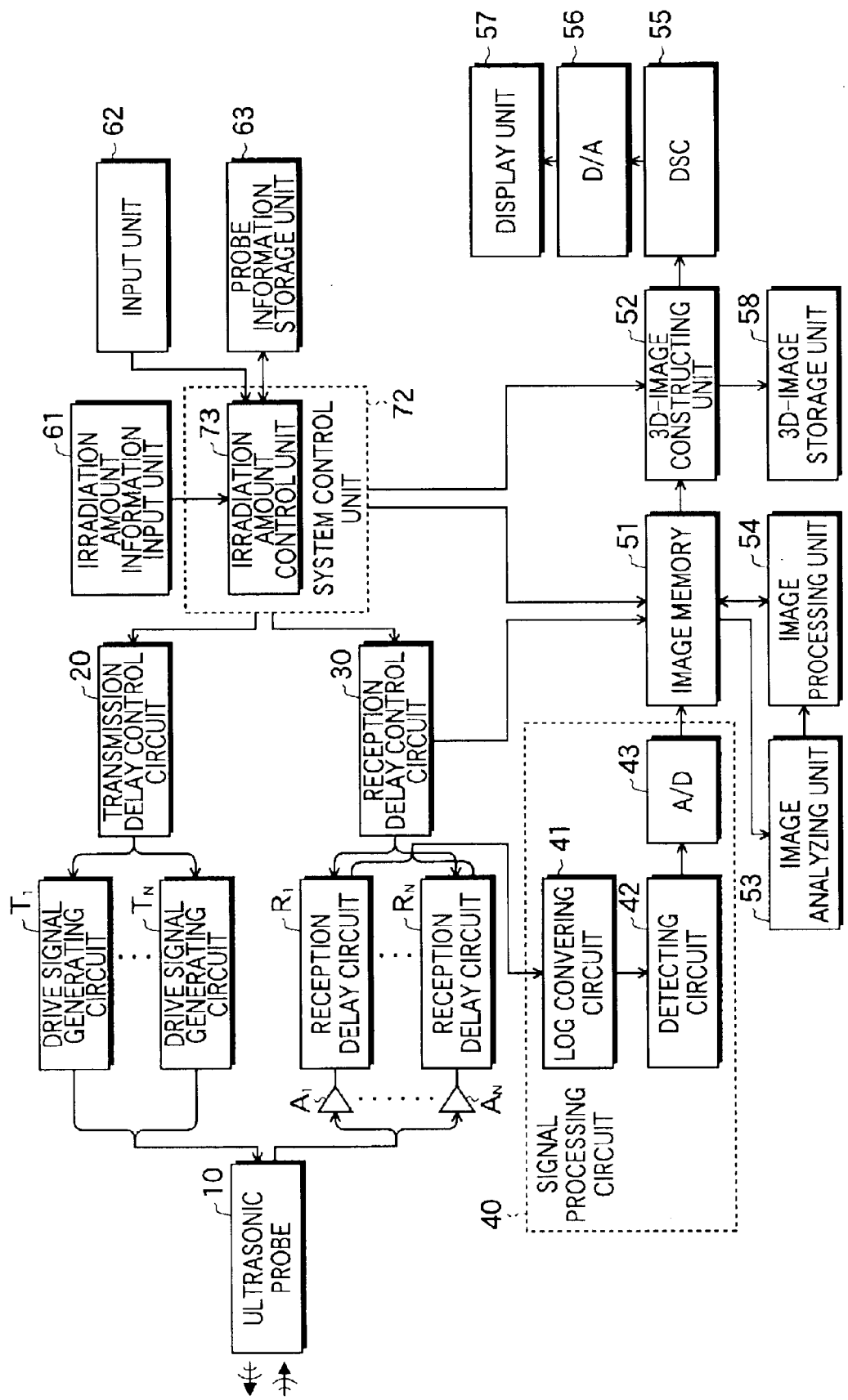
FIG. 4 is a block diagram for schematically showing an arrangement of an ultrasonic diagnosing apparatus according to a second embodiment of the present invention.

Next, an ultrasonic diagnosing apparatus according to a second embodiment of the present invention will now be described with reference to FIG. 4. FIG. 4 is a block diagram for schematically showing an arrangement of the ultrasonic diagnosing apparatus according to the second embodiment. As shown in FIG. 4, this ultrasonic diagnosing apparatus is provided with an input unit 62, a probe information storage unit 63 and a system control unit 72. Other structural elements of this ultrasonic diagnosing apparatus are similar to those of the ultrasonic diagnosing apparatus as shown in FIG. 1.

The input unit 62 includes an adjusting knob, an input mouse, a touch panel, a pointing device such as a light pen, and a keyboard, etc. This input unit 62 is employed when an instruction (command), information or the like is input into the system control unit 72.

The probe information storage unit 63 stores, in correspondence with each ultrasonic probe 10, a relationship between voltages applied to a plurality of ultrasonic transducers included in the ultrasonic probe 10 and irradiation intensity of ultrasonic waves transmitted from the ultrasonic probe 10 in accordance with the applied voltages. Such a relationship between the applied voltages and the irradiation intensity will be referred to as "probe information" hereinafter.

In this case, as the ultrasonic probe 10, various types of probes such as a concave type probe, a convex array type probe, and an annular type probe may be employed in addition to the linear array type probe as shown in FIG. 2. As a consequence, a relationship between voltages applied to an ultrasonic probe and intensity of ultrasonic waves transmitted in accordance with these applied voltages differs depending upon types of these ultrasonic probes and materials, sizes, and arrays of ultrasonic transducers employed in these ultrasonic probes. Under such a circumstance, in the second embodiment, a plurality of probe information corresponding to the respective ultrasonic probes are previously stored in the probe information storage unit 63, and proper probe information is selected in accordance with an ultrasonic probe to be used.

The system control unit 72 controls the respective structural units of the ultrasonic diagnosing apparatus according to the second embodiment. Also, the system control unit 72 includes an irradiation amount control unit 73. The irradiation amount control nit 73 adjusts the frame rate on the basis of the irradiation amount information and the probe information so as to control the irradiation amount of ultrasonic waves which irradiate the object to be inspected.

Figure 5:
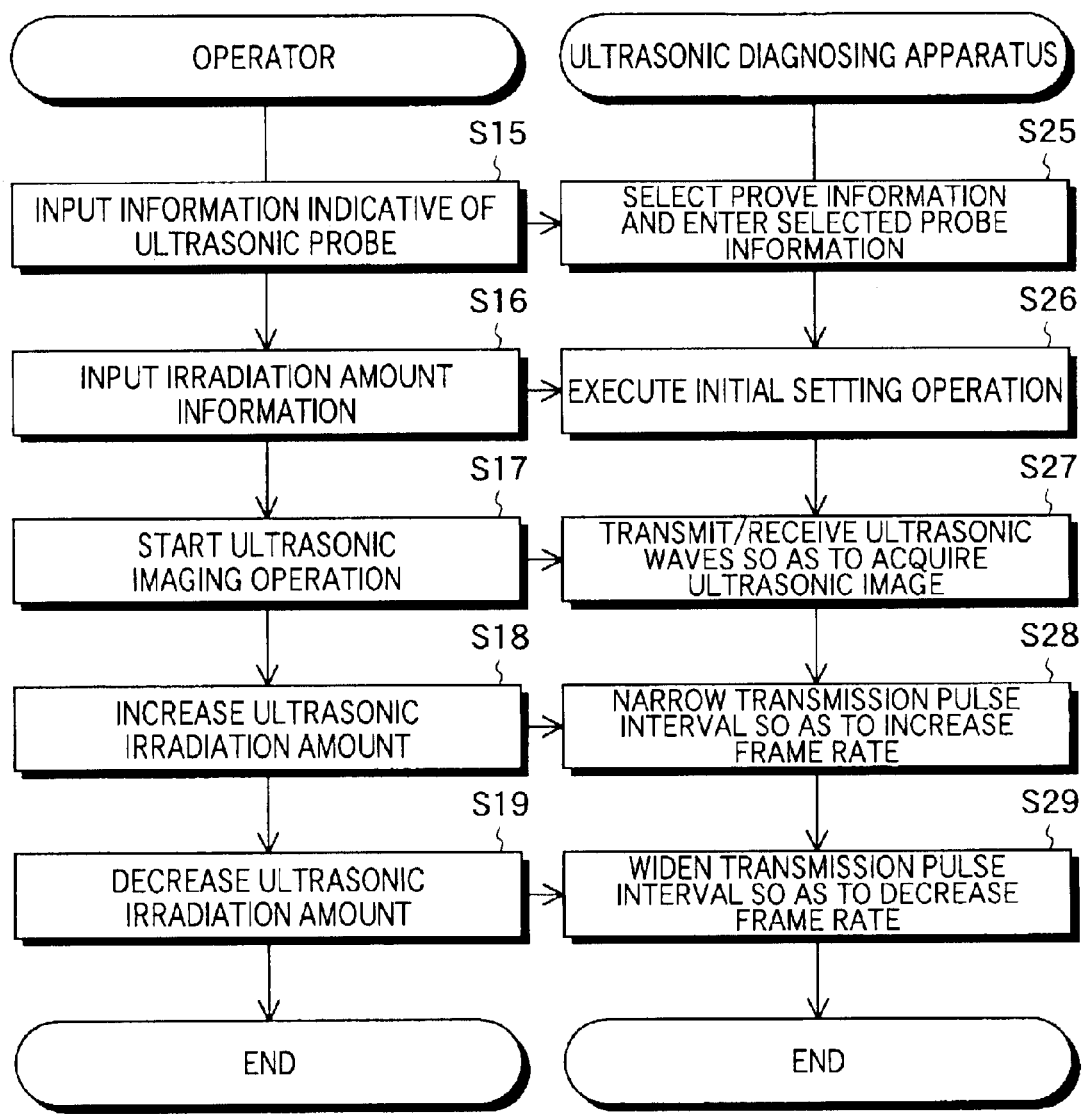
FIG. 5 is a flow chart for showing operations of the ultrasonic diagnosing apparatus according to the second embodiment of the present invention.

Referring now to a flow chart of FIG. 5, diagnosing operations of the ultrasonic diagnosing apparatus according to the second embodiment will be described. First, the operator inputs information indicative of an ultrasonic probe such as an ID of this ultrasonic probe by employing the input unit 62 at step S15. Alternatively, when an ultrasonic probe is connected to the main body of this ultrasonic diagnosing apparatus, the system control unit 72 may recognize such information indicative of this connected ultrasonic probe. At step S25, on the basis of the input information, the system control unit 72 of the ultrasonic diagnosing apparatus selects probe information corresponding to this ultrasonic probe from among a plurality of probe information stored in the probe information storage unit 63 and inputs this selected probe information into the irradiation amount control unit 73.

Next, the operator inputs irradiation amount information by using the irradiation amount information input unit 61 at step S16. In that time, similar to the first embodiment, it is preferable to set a value in accordance with the object to be inspected in such a manner that the ultrasonic irradiation amount becomes a minimum necessary irradiation amount. Alternatively, similar to the first embodiment, such information related to the object to be inspected, e.g., an age, a build and a body portion of the object which is irradiated by the ultrasonic waves may be input so that a proper value can be obtained.

At step S26, the irradiation amount control unit 73 of the ultrasonic diagnosing apparatus executes an initial setting operation on the basis of the input probe information and the input irradiation amount information. In other words, the irradiation amount control unit 73 obtains voltage values (V) to be applied to the ultrasonic transducers on the basis of the probe information and then outputs the obtained voltage values (V) to the circuits in a transmission system in order to transmit such ultrasonic waves having a predetermined irradiation intensity. Also, the irradiation amount control unit 73 obtains an irradiation amount of ultrasonic waves which irradiate the object to be inspected while the ultrasonic waves having this irradiation intensity is transmitted once. In this case, the ultrasonic irradiation amount in one irradiating operation can be obtained by integrating the irradiation intensity of ultrasonic waves by time. Furthermore, the irradiation amount control unit 73 sets a frame rate on the basis of both the irradiation amount information and the ultrasonic irradiation amount in one irradiating operation.

When the operator commences ultrasonic imaging operation at step S17, the ultrasonic diagnosing apparatus transmits ultrasonic waves and then receives ultrasonic echoes so as to acquire an ultrasonic image of an object to be inspected at step S27.

When the operator judges that a more precise ultrasonic image must be acquired, the operator adjusts the irradiation amount information input unit 61 so as to increase the ultrasonic irradiation amount at step S18. In response to this, the irradiation amount control unit 73 narrows the transmission pulse interval so as to increase the frame rate on the basis of the irradiation amount information at step S28.

On the other hand, the operator recognizes such a condition, namely, after the ultrasonic probe 10 has passed through a region where detailed image information is required, or while either a not-important region or a region which becomes risky when an ultrasonic irradiation amount to the object is large is scanned, the operator adjusts the irradiation amount information input unit 61 so as to decrease the ultrasonic irradiation amount at step S19. In response to this, the irradiation amount control unit 73 widens the transmission pulse interval on the basis of the irradiation amount information in order to lower the frame rate at step S29.

According to the second embodiment, since the frame rate is adjusted on the basis of the irradiation intensity corresponding to the ultrasonic probe which is used at that time, the irradiation amount of ultrasonic waves with respect to the object to be inspected can be more effectively and more correctly controlled.

Figure 6:
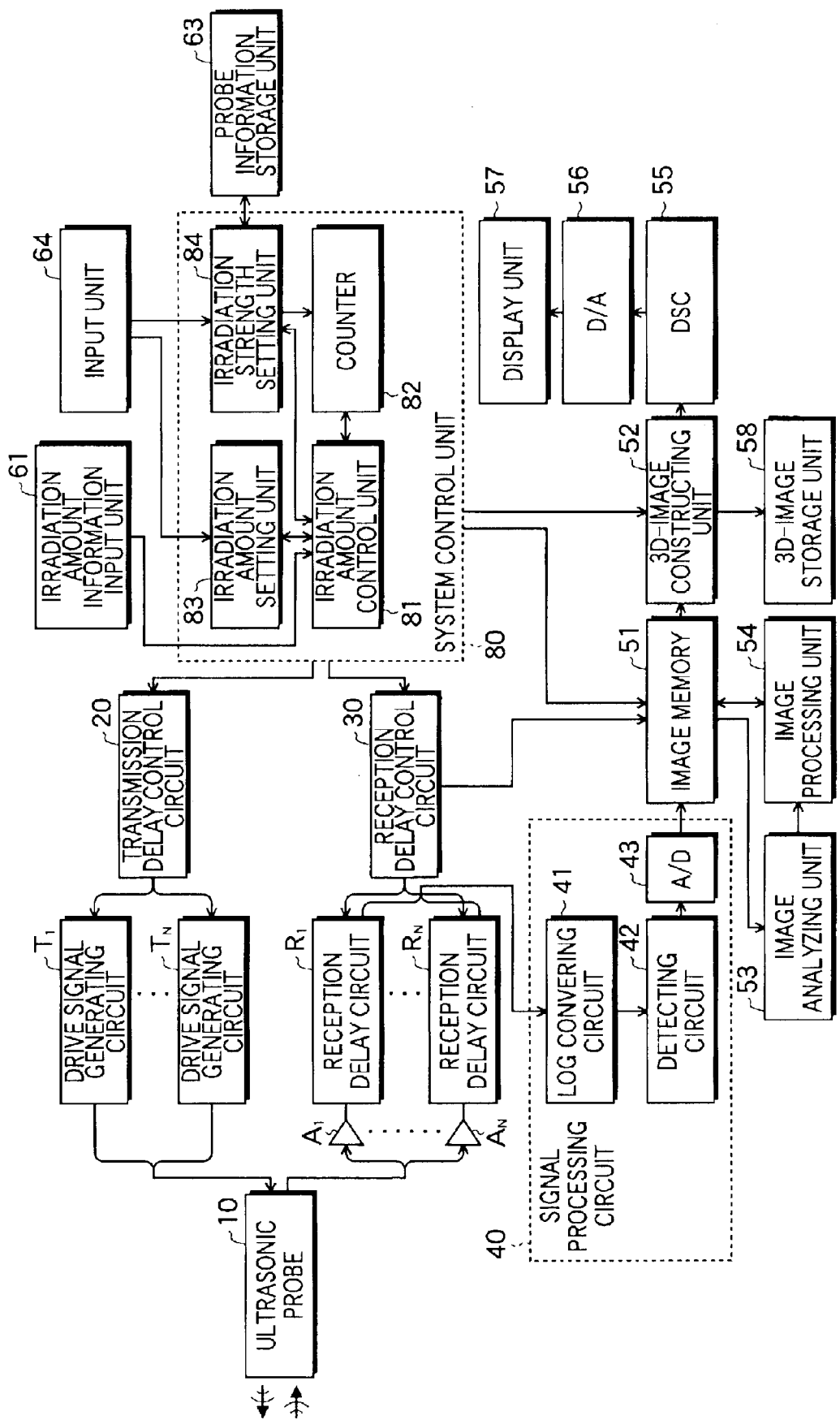
FIG. 6 is a block diagram for schematically showing an arrangement of an ultrasonic diagnosing apparatus according to a third embodiment of the present invention.

Next, an ultrasonic diagnosing apparatus according to a third embodiment of the present invention will now be described with reference to FIG. 6. FIG. 6 is a block diagram for schematically showing an arrangement of the ultrasonic diagnosing apparatus according to the third embodiment.

As shown in FIG. 6, this ultrasonic diagnosing apparatus is provided with an input unit 64, a probe information storage unit 63, and a system control unit 80. Other structural elements employed in this ultrasonic diagnosing apparatus are similar to those of the ultrasonic diagnosing apparatus as shown in FIG. 4.

The input unit 64 includes an adjusting knob, an input mouse, a touch panel, a pointing device such as a light pen, and a keyboard, etc. This input unit 64 is employed when an instruction (command), information or the like is input into the system control unit 80.

In the ultrasonic diagnosing apparatus according to the third embodiment, such information related to an ultrasonic irradiation amount is input via the input unit 64. This information includes a limit value of an ultrasonic irradiation amount, and information related to an ultrasonic irradiation intensity. The limit value of the ultrasonic irradiation amount implies a total value of ultrasonic irradiation amounts allowable to irradiate the object to be inspected. On the other hand, the information related to the irradiation intensity implies such information which is input by the operator in order to transmit ultrasonic waves having a predetermined irradiation intensity. As to the information related to the irradiation intensity, there are two cases, namely, one case where an operator inputs an irradiation intensity itself as, for example, sound pressure (Pa) and the other case where an operator inputs voltage values (V) applied to a plurality of ultrasonic transducers included in the ultrasonic probe 10.

In this case, the information related to the limit value of the ultrasonic irradiation amount and the information related to the irradiation intensity may be input by using a numerical value. Alternatively, information related to an object to be inspected (patient) such as an age, a build (physique), a body portion of the object which is irradiated by the ultrasonic waves or the like may be input so that both the limit value of the ultrasonic irradiation amount and the irradiation intensity can be calculated on the basis of the above-explained input information. In this alternative case, it is preferable to provide a storage unit for storing thereinto the information indicative of the limit values of the ultrasonic irradiation amounts and the irradiation intensity in correspondence to the information related to the objects to be inspected.

The probe information storage unit 65 stores thereinto a relationship between voltages applied to the ultrasonic probe 10 and intensity of the transmitted ultrasonic waves, that is, the probe information in correspondence with a plurality of ultrasonic transducers.

The system control unit 80 controls the respective structural units of this ultrasonic diagnosing apparatus. Further, the system control unit 80 includes an irradiation amount control unit 81, a counter 82, an irradiation amount setting unit 83 and an irradiation intensity setting unit 84.

The irradiation amount control unit 81 controls a frame rate so as to adjust an irradiation amount of ultrasonic waves transmitted toward the object to be inspected. The counter 82 accumulates an irradiation amount of transmitted ultrasonic waves, and monitors as to whether or not this accumulated value reaches a preset value. When the accumulated value of the ultrasonic irradiation amounts reaches the preset value in the counter 82, the irradiation amount control unit 81 changes the frame rate. The irradiation amount setting unit 83 sets an irradiation amount to the counter 82 on the basis of the limit value of the ultrasonic irradiation amount. Also, the irradiation intensity setting unit 84 sets voltage values, which is employed to transmit ultrasonic waves having such an irradiation intensity designated by the operator, on the basis of both the information indicative of the irradiation intensity and the probe information.

Figure 7:
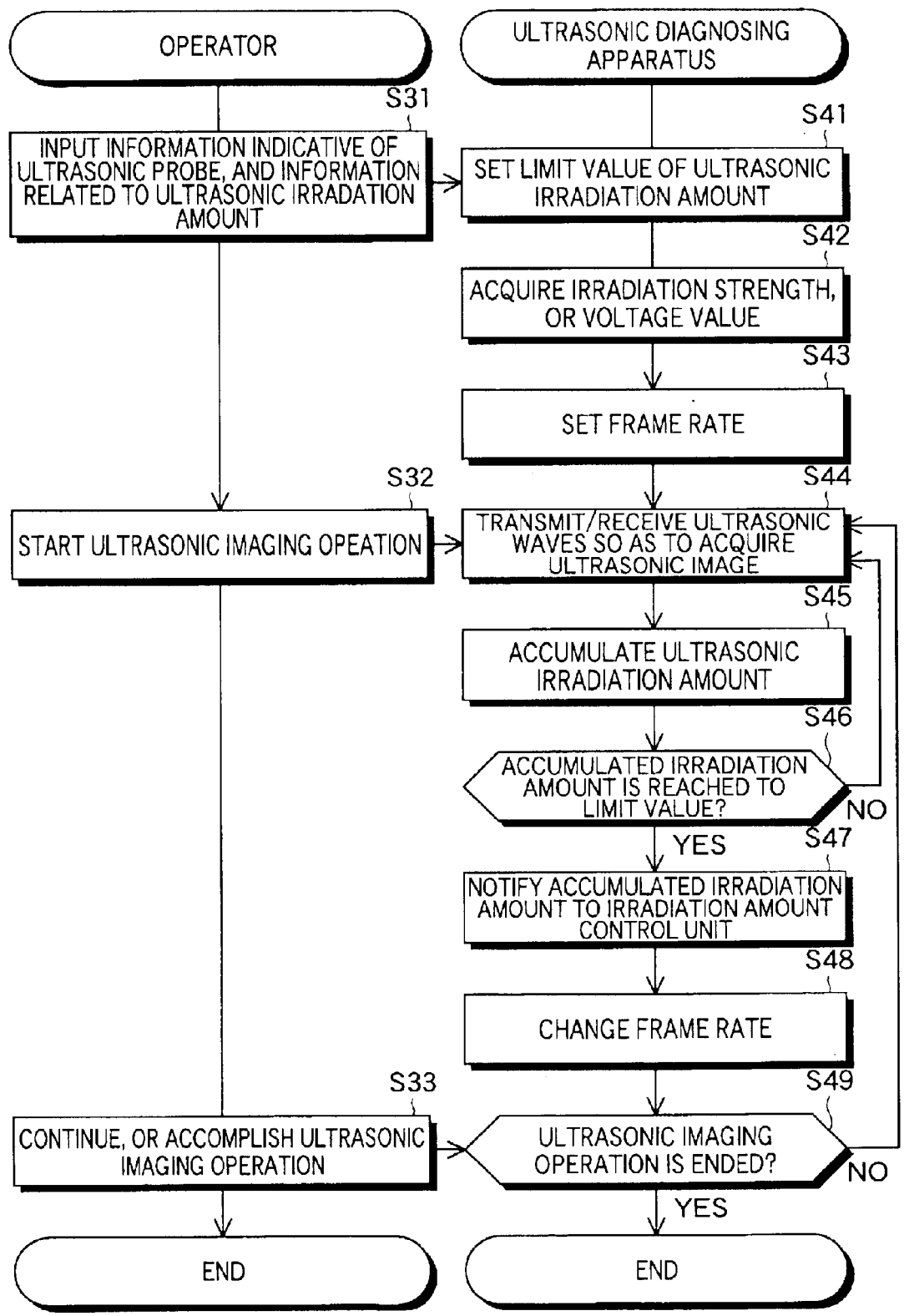
FIG. 7 is a flow chart for showing operations of the ultrasonic diagnosing apparatus according to the third embodiment of the present invention.

Referring now to a flow chart of FIG. 7, operations of the ultrasonic diagnosing apparatus according to the third embodiment will be described.

At step S31, the operator inputs information indicative of an ultrasonic probe to be used, a limit value of an ultrasonic irradiation amount and information related to an irradiation intensity by employing the input unit 64 of the ultrasonic diagnosing apparatus. Alternatively, when an ultrasonic probe to be used is connected to the main body of the ultrasonic diagnosing apparatus, the system control unit 80 may recognize such information indicative of the connected ultrasonic probe.

In accordance with this input information, the ultrasonic diagnosing apparatus executes an initial setting operation at steps S41 to S43. That is, at step S41, the irradiation amount setting unit 83 sets either the limit value of the ultrasonic irradiation amount input at step S31 or such a value which is obtained by multiplying this limit value by a predetermined ratio to the counter 82.

Further, at step S42, the irradiation intensity setting unit 84 selects the relevant probe information from a plurality of probe information stored in the probe information storage unit 65 on the basis of the information indicative of the probe. The irradiation intensity setting unit 84 calculates a value which is employed when ultrasonic waves are transmitted on the basis of this selected probe information and the information indicative of the irradiation intensity.

In the case where the information indicative of the irradiation intensity is input as an intensity value such as sound pressure (Pa), the irradiation intensity setting unit 84 obtains such voltage values (V) required to transmit ultrasonic waves having the input irradiation intensity on the basis of the relationship between the voltages to be applied and the intensity of ultrasonic waves to be transmitted, which are included in the probe information. This voltage value is input via the irradiation amount control unit 81 to the circuits of the transmission system. Also, the input irradiation intensity is set to the counter 82.

On the other hand, in such a case where the information indicative of the irradiation intensity is input as a voltage value (V), the irradiation intensity setting unit 84 obtains an irradiation intensity (Pa) of ultrasonic waves which are transmitted from the ultrasonic probe by applying thereto the input voltage value (V) on the basis of the relationship between the voltage to be applied and the intensity of ultrasonic waves to be transmitted, which are included in the probe information. The obtained irradiation intensity is set to the counter 82, and the input voltage value is output to the circuits in the transmission system.

At step S43, the irradiation amount control unit 81 sets a frame rate on the basis of both the limit value of the ultrasonic irradiation amount and the information indicative of the irradiation intensity. The irradiation amount control unit 81 may set the frame rate on the basis of input numerical value information. Alternatively, by previously forming a table for storing thereinto frame rates in correspondence with information related to objects, the irradiation amount control unit 81 may set the frame rate by referring to the table on the basis of the input information related to the object.

When the operator commences ultrasonic imaging operation at step S32, the ultrasonic diagnosing apparatus transmits ultrasonic waves on the basis of either the voltage value input at step S31 or the voltage value obtained at step S42, and receives ultrasonic echoes so that an ultrasonic image is acquired at step S44.

Also, when the ultrasonic imaging operation is commenced, the counter 82 starts to accumulate an ultrasonic irradiation amount at step S45. That is, the counter 82 integrates either the irradiation intensity input at step S31 or the irradiation intensity obtained at step S42 by time so as to obtain an ultrasonic irradiation amount in one irradiating operation, and accumulates the obtained ultrasonic irradiation amount.

The counter 82 continuously monitors as to whether or not the accumulated value of the ultrasonic irradiation amount reaches a preset value (step S46). At step S47, when the accumulated value of the ultrasonic irradiation amount reaches the preset value, the counter 82 notifies this fact to the irradiation amount control unit 81. In response to this notification, the irradiation amount control unit 81 changes the frame rate at step S48. As a method of changing a frame rate, the following frame rate changing methods may be conceived. For instance, in a method of reducing a frame rate, a changed frame rate may become a predetermined ratio (e.g., ½) of the frame rate before being changed. Alternatively, a frame rate is decreased by a predetermined ratio (for instance, every 10%) for a predetermined time period.

When the frame rate is changed, the operator can recognize that the ultrasonic irradiating amount reaches the preset value. Then, the operator may still continue the ultrasonic imaging operation under the lower frame rate, or may accomplish this ultrasonic imaging operation (step S33). Alternatively, if necessary for diagnostic purposes, the operator may increase the fame rate by employing the irradiation amount information input unit 61 or may change the irradiation intensity by employing the input unit 64 so as to continue the ultrasonic imaging operation. In the case where the operator continues the ultrasonic imaging operation, the process operation is returned from step S49 to step S44, this ultrasonic diagnosing apparatus performs the ultrasonic imaging operations while the ultrasonic irradiation amount is continuously accumulated.

Figure 8:
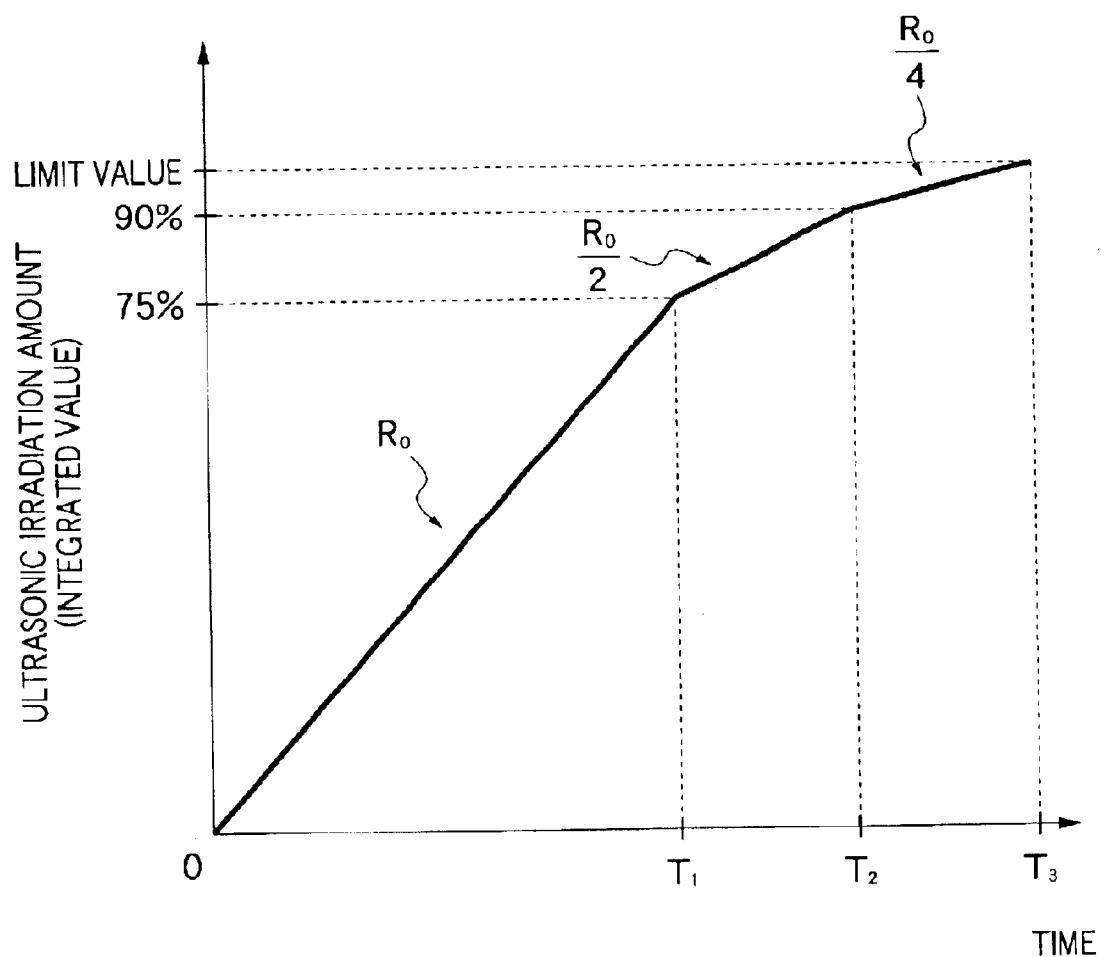
FIG. 8 is a graphic representation for showing an example method of changing a frame rate.

In the third embodiment, the frame rate is changed at step S48. Alternatively, when a total ultrasonic irradiation amount reaches the preset value, an alarm may be issued by way of voice and/or pictures, or a transmission operation of ultrasonic waves may be temporarily stopped. Also, in the case where the frame rate is changed at step S48, a preset value of the counter 82 may be changed in several steps in such a manner that if an accumulated value of ultrasonic irradiation amounts reaches a predetermined ratio with respect to a set limit value, then this frame rate is changed at stepwise manner. For instance, as shown in FIG. 8, after an ultrasonic imaging operation is commenced, an ultrasonic image of an object to be inspected is acquired in a firstly set frame rate $R_0$. After that, when an ultrasonic irradiation amount reaches 75% of a limit value at time point $T_1$, the frame rate $R_0$ may be decreased to a half of the firstly set frame rate, namely $R_0/2$. Further, when an ultrasonic irradiation amount reaches 90% of the limit value at time point $T_2$, the present frame rate $R_0/2$ is furthermore decreased to a half thereof, namely $R_0/4$. When an ultrasonic irradiation amount reaches the limit value at time point $T_3$, the transmission of the ultrasonic waves may be stopped. As previously explained, since the transmission pulse interval is carried out at stepwise manner in the ultrasonic diagnosing apparatus, the operator may predict a remaining amount of the ultrasonic irradiation amounts, and therefore, may execute the ultrasonic imaging operation in a schemed manner.

According to the third embodiment, while the ultrasonic irradiation amount with respect to the object is controlled, the ultrasonic imaging operations can be carried out in a desirable irradiation intensity.

Figure 9:
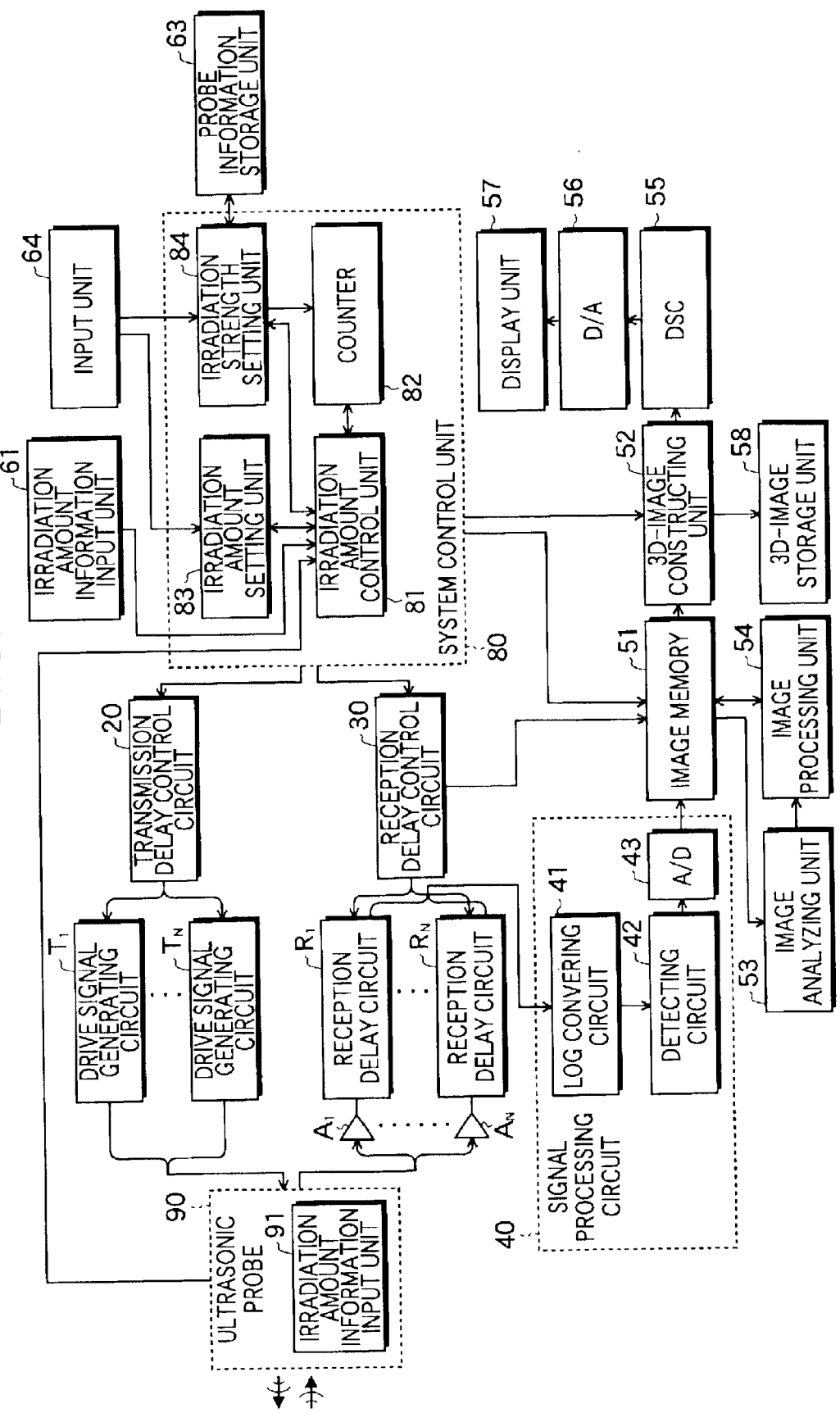
FIG. 9 is a block diagram for schematically showing an arrangement of an ultrasonic diagnosing apparatus according to a fourth embodiment of the present invention.

Next, an ultrasonic diagnosing apparatus according to a fourth embodiment of the present invention will now be described with reference to FIG. 9. FIG. 9 is a block diagram for schematically showing an arrangement of the ultrasonic diagnosing apparatus according to the fourth embodiment. This ultrasonic diagnosing apparatus according to the fourth embodiment is featured by that the irradiation amount information input unit 61 provided in the main body of the ultrasonic diagnosing apparatus as shown in FIGS. 1, 4 and 6 is provided in the ultrasonic probe.

As shown in FIG. 9, an ultrasonic probe 90 includes an irradiation amount information input unit 91. This irradiation amount information input unit 91 may be preferably realized by such an input device which may be manipulated by using a single hand of an operator, for instance, an adjusting knob, an adjusting button, or the like.

According to this embodiment, since the operator can adjust an ultrasonic irradiation amount by using his single hand when an object to be inspected is scanned by employing the ultrasonic probe 90, the operator can easily carry out the ultrasonic imaging operation. Although the fourth embodiment has been described as a modification of the ultrasonic diagnosing apparatus according to the third embodiment as shown in FIG. 6, the ultrasonic diagnosing apparatus according to the first or second embodiment may be similarly modified.

As previously described in detail, since the ultrasonic irradiation amount is controlled by adjusting the frame rate in the ultrasonic diagnosing apparatus according to the present invention, a total amount of ultrasonic waves which irradiate the object to be inspected for a fixed period of time can be reduced without deteriorating both the S/N ratio of the ultrasonic images and the image qualities per frame. As a consequence, the adverse influences caused by applying the ultrasonic waves to the object can be suppressed to the minimum allowable value so that safety performance required for the ultrasonic imaging operations can be improved.

What is claimed is:

1. An ultrasonic diagnosing apparatus comprising:
    ultrasonic transmitting and receiving means for transmitting ultrasonic waves in accordance with an applied voltage and receiving ultrasonic echoes reflected from an object to be inspected;
    input means for inputting information related to an irradiation amount of ultrasonic waves; and
    irradiation amount control means for adjusting a frame rate on the basis of the irradiation amount information input via said input means so as to control an irradiation amount of ultrasonic waves which irradiate the object.

2. An ultrasonic diagnosing apparatus according to claim 1, wherein said input means is coupled with an ultrasonic probe in an integral form.

3. An ultrasonic diagnosing apparatus according to claim 1, further comprising:
    storage means for storing thereinto a relationship between voltage values applied to said ultrasonic transmitting and receiving means and intensity of ultrasonic waves transmitted from said ultrasonic transmitting and receiving means in accordance with said voltage values, wherein:
    said irradiation amount control means obtains intensity of ultrasonic waves to be transmitted on the basis of the relationship between the voltage values and the intensity of ultrasonic waves, which is stored in said storage means, and obtains an irradiation amount of ultrasonic waves which irradiate the object on the basis of the obtained intensity of ultrasonic waves, thereby adjusts the frame rate on the basis of the obtained irradiation amount of ultrasonic waves.

4. An ultrasonic diagnosing apparatus according to claim 3, wherein said irradiation amount control means obtains the irradiation amount of ultrasonic waves by integrating the intensity of ultrasonic waves to be transmitted by time.

5. An ultrasonic diagnosing apparatus comprising:

ultrasonic transmitting and receiving means for transmitting ultrasonic waves in accordance with an applied voltage and receiving ultrasonic echoes reflected from an object to be inspected;

accumulating means for accumulating an irradiation amount of ultrasonic waves transmitted from said ultrasonic transmitting and receiving means to obtain an accumulated value; and irradiation amount control means for adjusting a frame rate on the basis of a relationship between the accumulated value obtained by said accumulating means and a preset value so as to control an irradiation amount of ultrasonic waves which irradiate the object.

6. An ultrasonic diagnosing apparatus according to claim 5, further comprising:

input means for inputting information which is employed to set an irradiation amount of ultrasonic waves; and setting means for setting the preset value related to the irradiation amount of ultrasonic waves on the basis of the information input via said input means so as to store the preset value into said accumulating means.

7. An ultrasonic diagnosing apparatus according to claim 6, further comprising:

storage means for storing thereinto a relationship between voltage values applied to said ultrasonic transmitting and receiving means and intensity of ultrasonic waves transmitted from said ultrasonic transmitting and receiving means in accordance with said voltage values, wherein:

said accumulating means obtains intensity of ultrasonic waves to be transmitted on the basis of the relationship between the voltage values and the intensity of ultrasonic waves, which is stored in said storage means, and obtains an irradiation amount of ultrasonic waves which irradiate the object on the basis of the obtained intensity of ultrasonic waves, thereby accumulates the obtained irradiation amount of ultrasonic waves.

8. An ultrasonic diagnosing apparatus according to claim 7, wherein said accumulating means accumulates the irradiation amount of ultrasonic waves obtained by integrating the intensity of ultrasonic waves to be transmitted by time.

9. An ultrasonic diagnosing apparatus according to claim 6, wherein said accumulating means accumulates the irradiation amount of ultrasonic waves obtained by integrating the intensity of ultrasonic waves to be transmitted by time.

10. An ultrasonic diagnosing apparatus according to claim 5, further comprising:

storage means for storing thereinto a relationship between voltage values applied to said ultrasonic transmitting and receiving means and intensity of ultrasonic waves transmitted from said ultrasonic transmitting and receiving means in accordance with said voltage values, wherein:

said accumulating means obtains intensity of ultrasonic waves to be transmitted on the basis of the relationship between the voltage values and the intensity of ultrasonic waves, which is stored in said storage means, and obtains an irradiation amount of ultrasonic waves which irradiate the object on the basis of the obtained intensity of ultrasonic waves, thereby accumulates the obtained irradiation amount of ultrasonic waves.

11. An ultrasonic diagnosing apparatus according to claim 10, wherein said accumulating means accumulates the irradiation amount of ultrasonic waves obtained by integrating the intensity of ultrasonic waves to be transmitted by time.

12. An ultrasonic diagnosing apparatus according to claim 5, wherein said accumulating means accumulates the irradiation amount of ultrasonic waves obtained by integrating the intensity of ultrasonic waves to be transmitted by time.

13. An ultrasonic diagnosing apparatus according to claim 5, further comprises:

second input means for inputting information related to an irradiation amount of ultrasonic waves, wherein:

said irradiation amount control means adjusts the frame rate on the basis of the information related to an irradiation amount of ultrasonic waves input via said second input means.

14. An ultrasonic diagnosing apparatus according to claim 13, wherein said second input means is coupled with an ultrasonic probe in an integral form.

* * * * *